US008499645B2

(12) United States Patent  
Chasiotis et al.

(10) Patent No.: US 8,499,645 B2
(45) Date of Patent: Aug. 6, 2013

(54) STRESS MICRO MECHANICAL TEST CELL, DEVICE, SYSTEM AND METHODS

(75) Inventors: Ioannis Chasiotis, Savoy, IL (US); Mohammad Naraghi, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 665 days.

(21) Appl. No.: 12/527,776

(22) PCT Filed: Feb. 20, 2008

(86) PCT No.: PCT/US2008/002223
§ 371 (c)(1),
(2), (4) Date: Dec. 9, 2009

(87) PCT Pub. No.: WO2008/123908
PCT Pub. Date: Oct. 16, 2008

(65) Prior Publication Data
US 2010/0088788 A1   Apr. 8, 2010

Related U.S. Application Data

(60) Provisional application No. 60/902,424, filed on Feb. 21, 2007.

(51) Int. Cl.
*G01N 3/06* (2006.01)
*G01N 3/04* (2006.01)

(52) U.S. Cl.
USPC .................................. 73/789; 73/856; 73/831

(58) Field of Classification Search
USPC ................. 73/788, 828, 831, 860, 862.391, 73/862.392, 862.636; 977/724, 725, 880, 977/881
See application file for complete search history.

(56) References Cited

U.S. PATENT DOCUMENTS 6,489,611 B1   12/2002   Aumond et al.
6,817,255 B2   11/2004   Haque et al.

(Continued)

OTHER PUBLICATIONS

M. A. Hague, M. T. A. Saif, "Application of MEMS force sensors for in situ mechanical characterization of nano-scale thin films in SEM and TEM," Sensors and Actuators A 97-98 (2002) 239-245.*

(Continued)

*Primary Examiner* — Lisa Caputo
*Assistant Examiner* — Punam Roy
(74) *Attorney, Agent, or Firm* — Greer, Burns & Crain Ltd.

(57) ABSTRACT

The invention provides a stress micro mechanical system for measuring stress and strain in micro- and nano-fibers tubes, and wires as well as for measuring the interface adhesion force and stress in nanofibers and nanotubes embedded in a polymer matrix. A preferred system of the invention has a substrate for supporting a MEMS fabrication. The MEMS fabrication includes freestanding sample attachment points that are movable in a translation direction relative to one another when the substrate is moved and a sample is attached between the sample attachment points. An optical microscope images surfaces of the MEMS fabrication. Software conducts digital image correlation on obtained images to determine the movement of the surfaces at a resolution much greater than the hardware resolution of the optical microscope. A preferred method for measuring stress and strain in micro- and nano-fibers, tubes, and wires, and/or measuring the force required to pull-out individual micro- and nano-fibers, tubes, and wires from a polymer matrix and to therefore measure interfacial adhesion is also provided. In the method a sample is attached between freestanding platforms in a MEMS device. Relative translational movement between the platforms is created and motion of the platforms is imaged with an optical microscope. Mechanical and adhesion properties of the sample are determined by applying a digital image correlation algorithm to the image data.

16 Claims, 6 Drawing Sheets

U.S. PATENT DOCUMENTS

| | | | | |
|---|---|---|---|---|
| 7,444,880 | B2* | 11/2008 | Zhang et al. | 73/779 |
| 7,752,916 | B2* | 7/2010 | Han et al. | 73/789 |
| 2004/0211271 | A1* | 10/2004 | Han et al. | 73/866.5 |
| 2008/0245140 | A1* | 10/2008 | Clark | 73/105 |
| 2009/0194689 | A1* | 8/2009 | Abramson et al. | 250/307 |
| 2010/0057381 | A1* | 3/2010 | Pardoen et al. | 702/42 |
| 2010/0224006 | A1* | 9/2010 | Pardoen et al. | 73/826 |
| 2011/0317157 | A1* | 12/2011 | Kang et al. | 356/244 |

OTHER PUBLICATIONS

Written Opinion of the International Searching Authority for PCT/US2008/002223, Sep. 17, 2008.*

E. Mazza, G. Danuser, and J. Dual, "Light optical deformation measurements in microbars with nanometer resolution," Microsystem Technologies 2 (1996) pp. 83-91.*

H.W. Schreier, D. Garcia, and M. A. Sutton, "Advances in Light Microscope Stereo Vision," Society for Experimental Mechanics vol. 44, No. 3, Jun. 2004 pp. 278-288.*

H. Ogawa, K. Suzuki, S. Kaneko, Y. Nakano, Y. Ishikawa, and T. Kitahara, "Measurements of mechanical properties of microfabricated thin films," Micro Electro Mechanical Systems, 1997. MEMS '97, Proceedings, IEEE., Tenth Annual International Workshop on, pp. 430-435, 26-30, Jan. 1997.*

D. Zhang, M. Luo, and D. D. Arola, "Displacement/strain measurements using an optical microscope and digital image correlation," Optical Engineering 45(3), 033605 (Mar. 2006).*

Shaoning Lu et al., "In situ Mechanical Testing of Templated Carbon Nanotubes", *Review of Scientific Instrument*, vol. 77, 2006, pp. 125101-1-125101-6.

Taechung YI et al., "Measurement of Mechanical Properties of MEMS Materials", *Measurement Science and Technology*, vol. 10, 1999, pp. 706-716.

Min-Feng Yu et al., "Tensile Loading of Ropes of Single Wall Carbon Nanotubes and their Mechanical Properties", *Physical Review Letters*, vol. 84, No. 24, Jun. 12, 2000, pp. 5552-5555.

Haque M A and Saif M T A, "A review of MEMS-based microscale and tensile and bending testing nanoscale", *J. Soc. Exp. Mech.*, vol. 43, 2003, pp. 248-255.

Inai R, Kotaki M and Ramakrishna S "Structure and properties of electrospun PLLA single nanofibers", *J. Nanotechnology*, vol. 16, 2005, pp. 208-213.

Jaecklin V P, Linder C, De Rooij N F, Moret J M, Bischof R and Rudolf F, "Novel polysilicon comb actuators for xy stages", *Journal of Microelectromechanical Systems* 92, 1992, pp. 147-149.

Kahn H, Ballarini R, Mullen R L and Heuer H, 1999 "Electrostatically actuated failure of microfabricated polysilicon fracture mechanics specimens", *Proc. R. Soc. Lond. A*, vol. 455, 1999, pp. 3807-3823.

Kiuchi M, Isono Y, Sugiyama S, Morita T and Matsui S, "Mechanical and electrical properties evaluation of carbon nanowire using electrostatic actuated nano tensile testing devices (EANAT)", *Proceedings of 2005 5th IEEE Conference on Nanotechnology*, Nagoya, Japan.

Knauss, Wolfgang G. et al., "Mechanical Measurements at the Micron and Nanometer Scales", *Mechanics of Materials*, vol. 35, 2003, pp. 217-231.

Lu S, Guo Z, Ding W and Ruoff R S, 2006 "Analysis of a microelectromechanical system testing stage for tensile loading of nanostructures",*J. Rev. Sci. Instrum.*, vol. 77, 2006, pp. 056103 (1-4).

Naraghi, Mohammad et al., "Mechanical Deformation and Failure of Electrospun Polyacrylonitrile Nanofibers as a Function of Strain Rate", *Applied Physics Letters*, vol. 91, 2007, pp. 1-1-1-4.

Naraghi, Mohammad et al., "Novel Method for Mechanical Characterization of Polymeric Nanofibers", *Review of Scientific Instruments*, vol. 78, 2007, pp. 085108-1-085108-7.

Samuel, B.A. et al., "Mechanical Testing of Pyrolysed poly-furfuryl alcohol nanofibres", *Nanotechnology*, vol. 18, 2007, pp. 115704-1-115704-8.

Tan E P S, Goh C N, Sow C H and Lim C T 2005 "Tensile test of a single nanofiber using an atomic force microscope tip", *Appl. Phys. Lett.*, vol. 86 2005, pp. 073115(1-3).

Tan E P S and Lim C T, "Mechanical characterization of nanofibers—A reivew", *J. Compos. Sci. Technol.*, vol. 66, 2006, pp. 1102-1111.

Tan E P S and Lim C T, "Nanomechanical testing of polymeric nanofibers", *Proc. of SPIE*, vol. 5852, 2005, pp. 849-855.

Tan E P S and Lim C T, "Novel approach to tensile testing of micro- and nanoscale fibers", *J. Rev. Sci. Instrum.*, vol. 75, 2004, pp. 2581-2585.

Torii A, Sasaki M, Hane K and Okuma S, "A method for determining the spring constant of cantilevers for atomic force microscopy", *J. Measu. Sci. Techno.*, vol. 7, 1996, pp. 179-184.

Vendroux, G. et al., "Submicron Deformation Field Measurements: Part 2. Improved Digital Image Correlation", *Experimental Mechanics*, vol. 38, No. 2, Jun. 1998, pp. 86-92.

Xu Q, Xu L, Cao W and Wu S, "A study on the orientation structure and mechanical properties of polyacrylonitrile precursors", *J. Polym. Adv. Technol.*, vol. 16, 2005, pp. 642-645.

Yu M F, Lourie O, Dyer M J, Moloni K, Kelly T F, Ruoff R S "Strength and breaking mechanism of multi-walled carbon nanotubes under tensile load", *J. Science*, vol. 287 2000, pp. 637-640.

Zhu Y, Moldovan N and Espinosa H D, "A microelectromechanical load sensor for in situ electron and x-ray microscopy tensile testing of nanostructures", *Appl. Phys. Lett.*, vol. 86, 2005, pp. 013506(1-3).

Zussman E, Chen X, Ding W, Calabri L, Dikin D A, Quintana J P and Ruoff R S, "Mechanical and structural characterization of electrospun PAN-derived carbon nanofibers", *J. Carbon*, vol. 43, 2005, pp. 2175-2185.

Zussman E, Burnman M, Yarin A L, Khalfin R and Cohen Y, "Tensile deformation of electrospun nylon-6,6 nanofibers", *cJ. Polym. Sci., Part B: Polym. Phys.*, vol. 44, 2006, pp. 1482-1489.

* cited by examiner

STRESS MICRO MECHANICAL TEST CELL, DEVICE, SYSTEM AND METHODS

PRIORITY CLAIM AND REFERENCE TO RELATED APPLICATION

The application claims priority under 35 U.S.C. §119 from prior provisional application Ser. No. 60/902,424, which was filed Feb. 21, 2007.

STATEMENT OF GOVERNMENT INTEREST

This invention was made with government support under Contract DMI 0532320 awarded by National Science Foundation. The government has certain rights in the invention.

FIELD

A field of the invention is materials testing, and particularly nanofiber testing. Another field of the invention is micro devices, and particularly micro elecromechanical devices (MEMS).

BACKGROUND

Polymeric nanofibers are an emerging class of building block materials with applications in tissue engineering, filtration and nanocomposites. They are fabricated by a number of different processes, all of which can produce significant batch to batch differences. These fabrication processes include drawing, template synthesis, and electrospinning. Slight variations in the fabrication conditions and the large surface-to-volume ratio of individual nanofibers can produce batch to batch variations in the mechanical properties of the nanofibers that are produced.

The batch to batch variation greatly limits end uses of the nanofibers, which are often expected to perform critical functions in their end uses. Characterization of the mechanical properties of a batch of nanofibers can provide the necessary assurance that a particular batch of nanofibers is suited for their end uses. Determining nanofiber mechanical properties is not a straightforward task, primarily due to their very small dimensions and fragility. Practical testing methods and apparatuses that fit within the nanofiber manufacturing scheme are lacking.

Tension tests are best suited to testing of polymeric nanofibers because the fibers can only bear tensile forces well. Compared to other methods, such as nanoindentation and bending, tension tests require very few assumptions to extract mechanical properties, and tension tests allow for the application of a range of strain rates including creep and stress relaxation. With suitable tension testing schemes and devices lacking, attempts have been made to use other tests, e.g., nanoindentation, bending, and resonance frequency measurements, to obtain nanofiber mechanical properties. At best, these techniques provide results that are qualitative. Such testing techniques also fail to conform to standard set by the American Society for Testing and Materials) (ASTM). The ASTM approved method of evaluating the mechanical behavior of materials is tension testing.

Tension testing of nanofibers, nanotubes and nanowires has generally been conducted with the assistance of Atomic Force Microscopy (AFM) cantilevers and examined with a scanning electron microscope (SEM). A common setup involves one AFM cantilever or two opposing AFM cantilevers for mounting nanofibers. The AFM cantilever(s) serve the dual role of a load-measuring element and displacement sensor. A load is applied by deflection of the AFM cantilever, typically inside an SEM, which records the deflection of the AFM cantilever. Strain in the nanofiber/nanowire is measured by monitoring variations in the distance between the AFM cantilever tip and the substrate, or by tracking distinct features on the sample during the test. The force in the sample is calculated by multiplying the deflection and bending stiffness of the AFM cantilever.

Both the AFM cantilever and the SEM microscope place substantial limits on such tension testing techniques. Since the AFM is used to create displacement and as the force sensor, relative error is increasing when the stiffness of the cantilever is substantially different than that of the nanofibers being tested. Using an SEM is cumbersome, and use of an optical microscope is difficult due to the limited depth of field and the associated out-of-plane motion of the AFM cantilevers.

Some all-MEMS (micromechanical systems) test cells have been proposed as such platforms that can be fabricated in large quantities and at low cost. On-chip actuators are several times smaller than external actuators, and they fit conveniently inside an electron microscope. These devices have also had a limited range of force and displacement and are, therefore, poorly suited for use with strong and/or elastic nanofibers, some of which stretch by several tens of microns.

As suitable tension tests have been lacking for such fibers, different approaches have been attempted. These include nanoindentation, bending tests, resonance frequency measurements, and microscale tension tests. Nanoindentation lacks great accuracy due to uncertainties regarding the nanoindenter tip shape and the relative tip-fiber configuration, the effect of fiber surface curvature and roughness, and the adhesion force between the sample and the indenter. The local measurement provided by indentation is a poor predictor of the behavior of nanofibers during axial stretching, which is of paramount concern in many nanofiber applications. Three-point-bending and cantilever bending tests provide some information about nanofiber/nanowire elastic response and yield point, but the precise definition of boundary conditions at the nanofiber scale is unknown. These types of tests also fail to account for fiber sliding and rotation that are likely to occur at points of contact with the nanofiber during testing. Resonance frequency measurements have been successful for stiff metallic and ceramic nanowires, but polymeric fibers, with their high elasticity make extension of this technique non trivial since polymeric fibers can exhibit a whipping motion under the lateral excitation applied in such tests. The resonance of an AFM cantilever has also been used to calculate fiber stiffness, but this approach is similarly limited for highly elastic fibers.

Thus, efforts continue to be directed toward developing a useful tension test for highly deformable and or strong nanofibers and nanowires. Most efforts have used MEMS actuators that have limited range of motion, and many have utilized SEM for imaging, which have the drawback discussed above. Recently, Samuel et al reported on mechanical testing of pyrolyzed polymer nanofibers with a microdevice that included a leaf-spring loadcell that was actuated externally with a piezomotor. Samuel B A, Hague M A, Yi B, Rajagopalan R and Foley H C 2007 J. nanotechnology 18 1-8. An SEM was used for high magnification imaging to measure displacements. The displacement of a point (pixel) is measured in this technique, limiting the resolution to the pixel level. The speed of measurement with the technique reported by Samuel et al requires minutes to collect a datum point in a stress-strain curve, making their approach inappropriate for testing materials that are subjected to creep and stress relaxation, such as polymers and metals. In addition, the range of fiber deformation by the method of Samuel et al is limited to a few microns.

SUMMARY OF THE INVENTION

The invention provides a stress micro mechanical system for measuring stress and strain in micro- and nano-fibers tubes, and wires, as well as for measuring the interface adhesion force and stress in nanofibers and nanotubes embedded in a polymer matrix. A preferred system of the invention has a substrate for supporting a MEMS fabrication. The MEMS fabrication includes freestanding sample attachment points that are movable in a translation direction relative to one another when the substrate is moved and a sample is attached between the sample attachment points. An optical microscope images surfaces of the MEMS fabrication. Software conducts digital image correlation on obtained images to determine the movement of the surfaces at a resolution much greater than the hardware resolution of the optical microscope. A preferred method for measuring stress and strain in micro- and nano-fibers, tubes, and wires, and/or measuring the force required to pull-out individual micro- and nano-fibers, tubes, and wires from a polymer matrix and to therefore measure interfacial adhesion is also provided. In the method a sample is attached between freestanding platforms in a MEMS device. Relative translational movement between the platforms is created and motion of the platforms is imaged with an optical microscope. Mechanical and adhesion properties of the sample are determined by applying a digital image correlation algorithm to the image data.

DETAILED DESCRIPTION OF THE PREFERRED EMBODIMENTS

Figure 1:
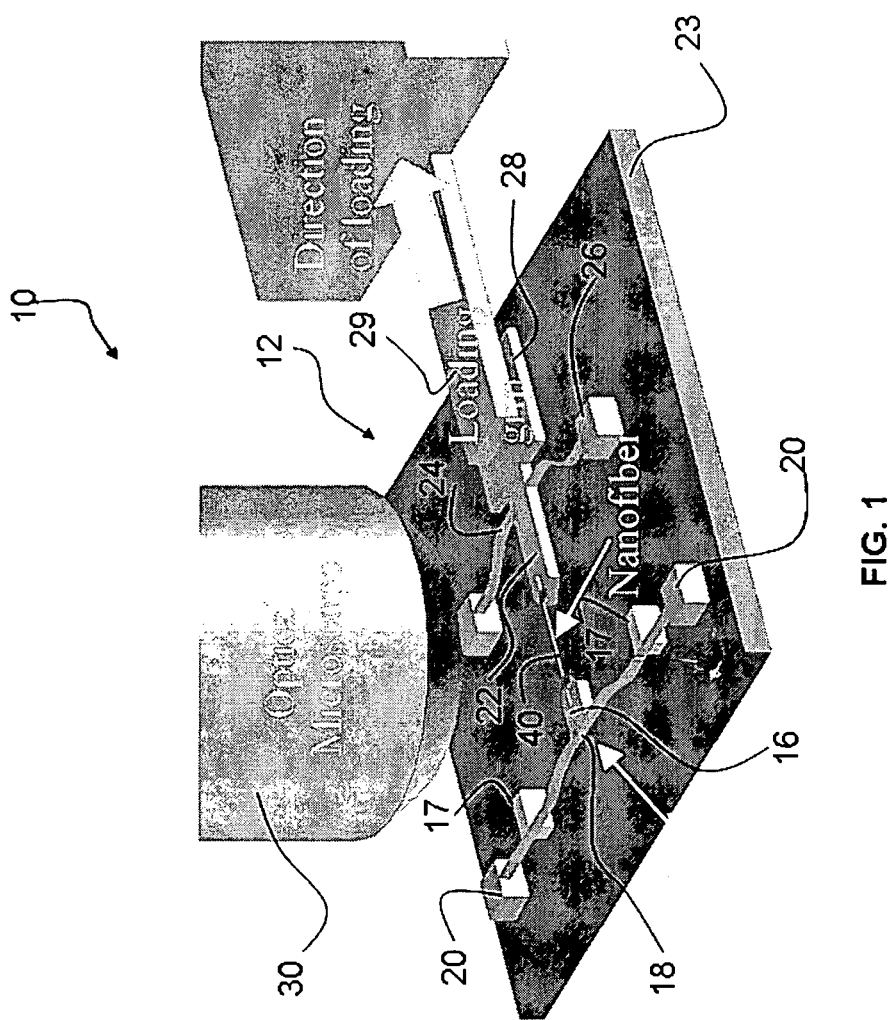
FIG. 1 shows a preferred embodiment micromechanical system for testing stress and strain of the invention.

The invention provides micromechanical test cell, test system and testing methods. Embodiments of the invention are useful, for example for testing mechanical properties and adhesion testing of single nano- and micro-fibers at various loading rates, as well as for testing of nanowires and nanotubes.

An embodiment of the invention is a system for testing. The system includes a test cell in the form of a stress micro device formed by MEMS fabrication. The test cell is configured to apply stress to a nano- or micro-fiber, tube or wire. The motion of substantial portions of surfaces of the stress micro device is captured by an optical microscope with a high magnification objective in combination and analyzed with a digital image correlation algorithm. Data acquired during testing are analyzed to provide mechanical properties and/or adhesion properties of the elongated nano- or micro-sample being tested.

A test cell of the invention is useful for measuring stress and strain in micro and nanofibers, wires and tubes. A test cell of the invention is also useful for measuring the force required to pull-out individual micro- and nano-fibers, tubes, and wires from a polymer matrix and therefore measure interfacial adhesion. A preferred test cell includes a substrate for supporting a MEMS fabrication. A MEMS fabrication on the substrate includes a leaf spring anchored to the substrate to support first free-standing platform for gripping a first end of an elongated nano- or micro-sample to be tested. A second free-standing platform supported by another spring that is anchored to the substrate holds a second end of the sample. An actuator, for example an external actuator, creates relative translation movement of the first and second free-standing platforms away from each other to impart tension upon the sample.

Methods and devices of the present invention enable accurate tensile testing of soft nanofibers. While most work has assumed that small fibers, such as nanofibers, should be tested in an electron microscope, the present inventors have discovered and addressed problems with tensile testing conducted in electron microscopy. One problem discovered by the inventors is that the electron beam and vacuum environment of an electron microscope alters the material properties of many organic nanofibers that are of interest for tensile testing. Another problem discovered by the inventors is that, while an electron microscope is a powerful instrument and its use naturally suggests the best method for measuring small movements, the point movement measurements conducted in the electron microscope place a limit on the resolution of movement and rate of movement that can be measured. Similarly, optical microscope methods that track a point or a number of points as pixels and measurement displacement are limited in the resolution of the measurement that can be obtained. Methods and devices of the invention are capable of providing better resolution than such point (pixel) movement measurements. Systems and methods of the invention provide a sub-pixel resolution measurement using an optical microscope and a digital image correlation calculation. A surface of the test cell is imaged and the movement of a portion of the surface test cell is tracked in a manner that permits rigid body motions to be resolved from optical images with an accuracy of a few tens of nanometers by the application of digital image correlation (DIC). The surface portion of the test cell used preferably has markings or irregularities that facilitate the measurement and DIC. An accuracy of ~50 nm displacement simply by using optical images can be achieved, which is about a tenth of the wavelength of visible light.

In systems of the invention, fiber elongation and tensile force can be obtained simultaneously and independently from optical measurements processed by DIC computer program that measures portion of the surface of the test cell to achieve measurement of sub-pixel resolution. Using an optical microscope in an open air environment that does not harm the nanofibers being tested, methods and devices of the invention can achieve resolution in displacements beyond the optical diffraction limit of the optical microscope and are capable of high strain resolution: Devices and methods of the invention use a continuous surface measurement via digital image correlation. Stress-strain curves can be obtained that are smooth and contain a large number of data points from tests that have large fiber deformations. Methods and devices of the invention can also calculate off-axis loads from full-field displacements. Additionally, with use of the external actuator, many rates of strain can be tested.

Large axial displacements for testing elastic nanofibers can be achieved with a test cell used in methods and systems of the invention. Preferred test cells can impart large strains/displacements and μN to sub-mN forces. Test cells of the invention can be fabricated by surface micromachining. Free standing platforms in test cells of the invention have ends configured as sample grips to hold a nanofiber, a leaf-spring for stretching of the fiber, and a grip for actuation by an external piezoelectric transducer (PZT).

Preferred methods of the invention include tuning the test cell stiffness with the aid stoppers, for example Gallium stoppers deposited by Focused Ion Beam (FIB) deposition. Test cells can be set up with stoppers to increase the accuracy in force measurement from polymeric nanofibers or other samples with a range of diameters. Devices of the invention can have a test cell with a particular predetermined stiffness set by the MEMS relative thickness and dimensions, and multiple devices on a single substrate will have highly similar stiffness. Additionally, after fabrication the test cell stiffness can be calibrated and tuned. Tuning can be accomplished with post fabrication stoppers.

An embodiment of the invention provides a method for measuring stress and strain in micro- and nano-fibers and other samples. In the method, a sample is attached between free standing platforms in MEMS test cell. Relative translational movement between the free-standing platforms is caused. Motion of platform surfaces is observed with an optical microscope and image data are acquired. Mechanical and/or adhesion properties of the sample are determined by applying a digital image correlation algorithm to the image data.

Preferred embodiment systems for testing can be used to study the mechanical behavior of many materials, including for example, single-walled and multi-walled carbon nanotubes, metallic nanowires, polymeric nanofibers with several hundreds of a percent stretch ratio, collagen fibrils, etc. by using a high magnification optical microscope for strain and stress measurement. Mounting of fibers thinner than 200 nm can be accomplished by dying the nanofibers with fluorescent dyes, and by using a fluorescent optical microscope to assist placement of the fibers. The length of materials to be tested can be on the order of 10-100 microns. Testing can be conducted at virtually any loading rate (speed) and temperature. Stress and strain can be simultaneously measured by systems of the invention and with high resolution. Instead of measuring the fiber motion from photographs, the motion of large portions of the test cell are calculated using a digital image correlation algorithm. Systems and devices of the invention have the ability to record time dependent mechanical behavior: A pair of applied force and fiber deformation values can be directly extracted from each image. Since force and deformation data are recorded simultaneously, this mechanical property test cell can be used to measure the behavior of fibers that are loaded at very fast rates. Systems and devices of the invention also account for different fiber gage lengths: Test cells of the invention can be fabricated to permit the fiber gage length to be adjusted from 10-100 microns, or more. Systems and methods of the invention provide the capability to test nanofibers that give very large stretch ratios: Such stretch ratios are typical of soft polymeric nanofibers produced by electrospinning, for example.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIG. 1 shows a preferred embodiment micromechanical system 10 for testing stress and strain. The system 10 is capable of performing nanoscale mechanical characterization of highly deformable nanofibers via optical microscope imaging and digital image correlation of surface movement. The system 10 includes a MEMS test cell 12. The test cell 12, illustrated schematically in FIG. 1B, includes a first platform 16 that is biased by a first leaf spring 18 that terminates at posts 20. A second platform 22 is biased by a second leaf spring 24 that terminates at posts 26. The leaf springs 18 and 24 are each formed by straight beams, which are each anchored onto the substrate 23 at one end by the respective posts 20, 26, and attached to a freestanding platform 16, 22, each of which having an end that acts as a freestanding grip for mounting a nanofiber. A sample, such as a nano- or micro-fiber or wire can be mounted via adhesive to ends of the platforms 16 and 22 that serve as grips.

The test cell 12 can be precisely tuned with the aid of one or more stoppers 17, which can be formed via focused ion beam deposition of Gallium, for example. Gallium is a preferred material as it is relatively easy to make a Gallium liquid metal ion source in a Focused Ion Beam (FIB), and Gallium adheres well to silicon, which is a preferred substrate material as it is widely used in the MEMS industry. However, artisans will appreciate that other substrate materials and stopper materials can be used in the MEMS fabrication. Instead of single crystal silicon, for example, the substrate could be glass, quartz. Also, the single crystal wafer could also be coated with Silicon Nitride. The second platform extends to include a surface 28 configured to attach to an external grip that is fixed on a three-axis precision translation stage, for example a tipless AFM cantilever 29 that is illustrated in FIG. 1.

The MEMS test cell 12 is illustrated as having single set of complementary first and second platforms 16 and 22, which are preferably formed on a single substrate 23. However, preferred embodiments include a plurality of test cells 12 formed on larger single substrates and that are manufactured at the same time. On a single substrate, MEMS test cells formed by the same process will have highly similar characteristics, which minimizes the need for calibration and provides consistent results for tests carried out on multiple test cells that were formed on the same substrate.

Referring to FIG. 1, a nanofiber mounted between the first and second platforms 16 and 22 undergoes a tension test that is imaged by an optical microscope 30. The optical microscope 30 has a field of view that encompasses both ends of the first and second platforms that secure the fiber, and their range of movement, and preferably the entirety of the first platform. Generally, the field of view of the optical microscope 30 encompasses a sufficient amount of platform surface area to enable digital image correlation to compute sub-pixel movement. To conduct the test, an external actuator (not shown) such as a piezoelectric actuator, pulls on grips, which can be the posts 20 or another grip mounted on the substrate, to translate the substrate 23 away from the AFM tipless cantilever 29. During a test, the second freestanding platform 22 that grips one end of a fiber 40 undergoing a test is held stationary and the substrate 23 is translated by an external actuator. The reverse operation or any actuation that creates controlled relative movement that imparts tension to the fiber by causing the distance of the first and second platforms 16 and 22 to increase can also be used.

Figure 2:
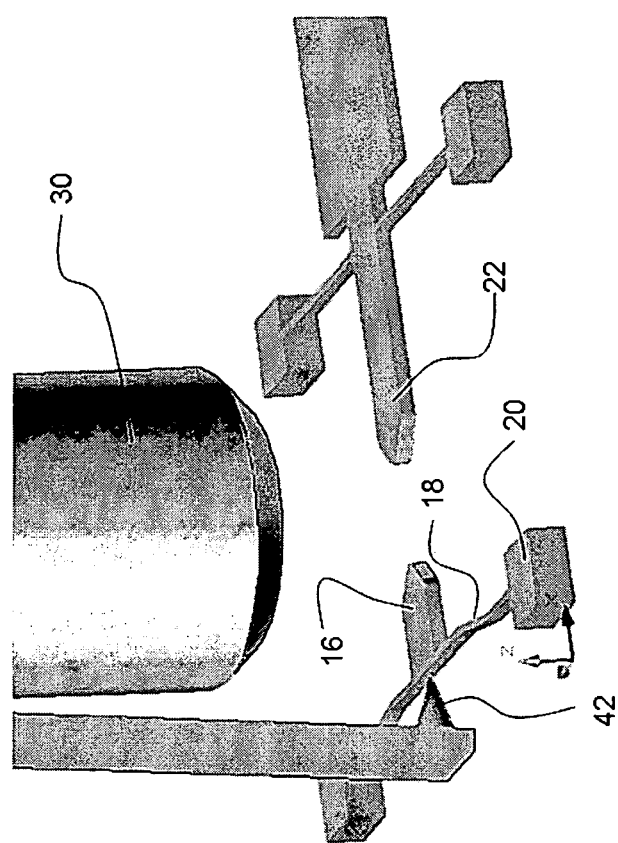
FIG. 2 illustrates a preferred method of calibrating a micromechanical system of the invention.

As illustrated in FIG. 2, test cells of the invention can be precisely calibrated, for example using an AFM cantilever with its attached tip 42. With an AFM cantilever with attached tip 42, the position of stoppers 17 (see FIG. 1) can be determined to set a particular spring resistance in a test cell 12. The stiffness can be determined by pushing the spring 18 laterally the AFM cantilever 42 that has precisely known stiffness (the stiffness of the AFM cantilever 42 can be accurately determined by analyzing the frequency spectrum of the cantilever's thermal fluctuations using an AFM), and recording the displacement of the platform 16 with the optical microscope 30 (or an SEM microscope) and of the AFM cantilever 42. The nominal stiffness of the AFM cantilever 42 should be close to the nominal value of the spring 18 stiffness to minimize the uncertainty in this measurement. See, Torii A, Sasaki M, Hane K and Okuma S 1996 "A method for determining the spring constant of cantilevers for atomic force microscopy." *J. Measu. Sci. Techno.* 7 179-84. The nominal stiffness of the test cell, k, can be calculated as $$k = \frac{24EI}{l^3}$$

where E, I, and l are elastic modulus of the material comprising the test cell, the moment of inertia of the test cell spring 18 cross section, and the length of each half of the spring (beam extending from the anchor 20 to the platform 16) of the test cell, respectively. Adjustments can be made by depositing stoppers 17 with a FIB.

The test cell of FIG. 1 permits submicron scale tensile tests to be performed in ambient conditions in open air under the optical microscope 30. The image of the optical microscope is acquired by any conventional devices (i.e. a CCD camera) and provided to software of the invention. Engineering stresses and strains can be obtained directly from the obtained digital images by extracting the relative rigid body displacements of the device components by digital image correlation (DIC). The accuracy in determining displacements by this optical method in experiments to demonstrate the invention was shown to be better than 50 nm.

A test is recorded optically, for example, using a CCD camera at 500× optical magnification (the selected magnification depends on the size of the device.) Digital images of the test cell are then processed using Digital Image Correlation (DIC) software to calculate the extension of the nanofiber and the deflection of the test cell springs that are then converted into strain and stress in the fiber as explained in detail below. The attachment of the sample to the grips is preferably accomplished using a viscous adhesive appropriate for the particular fiber material being tested. Other manners of attachment can be used, so long as sliding of the fiber on the grips is avoided during testing.

Figure 3:
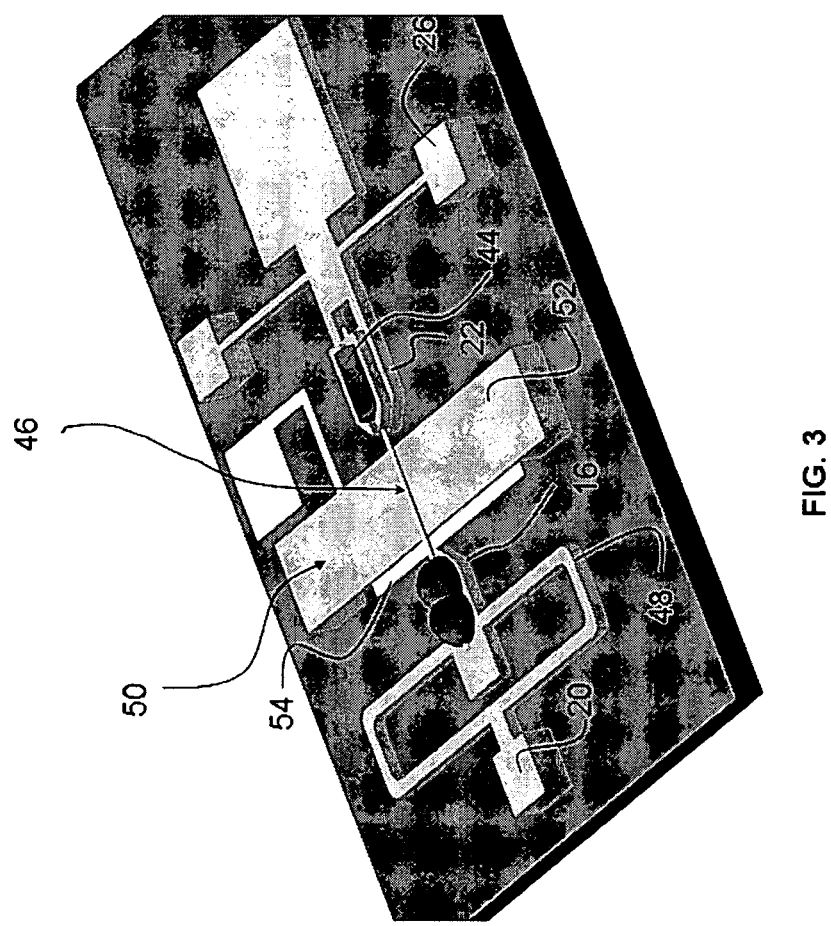
FIG. 3 illustrates a portion of another preferred embodiment micromechanical system for testing stress and strain.

Another type of test cell 42 is illustrated in FIG. 3. Like parts in FIG. 3 are identified with the same reference numbers used FIG. 1. In this embodiment, a polymer reservoir 44 on the second platform 22 hosts one end of a nanofiber 46 (or nanotube) for measuring the adhesion force between a nanofiber and a polymer in reservoir 44, which would be termed a fiber pull-out test. Part of the nanofiber or tube 46 is extended outside the reservoir 44 and the other end of the fiber is gripped by the first platform 16. The first platform is suspended by a generally u-shaped spring 48, which can provide up to twice the resolution in load measurement compared to the FIG. 1 embodiment. The two arms of the U-shaped spring 48 move in opposite directions and, therefore, for a given applied force, it is possible to measure twice the deflection.

The test cell 42 also includes an on-substrate AFM imaging support platform 50 for allowing imaging of the fiber by using an Atomic Force Microscope (AFM). The imaging support platform 50 is a capacitively actuated platform 52 and a bottom electrode 54. The actuator 50 can serve as a support to conduct imaging of the fiber by using an Atomic Force Microscope (AFM). Before the tension test or a fiber pull-out test where the interfacial strength between a micro-, nano-fiber, tube or wire and a polymer in reservoir 44 is measured, the fiber sample is mounted between the first and second platforms 16 and 22 with its gage section laying on the capacitively actuated platform 52. During a tension test, this platform 52 is deflected downwards capacitively by the application of a bias voltage. It is automatically restored to its original position (by spring back) when imaging by AFM is conducted. During a tension test, a bias voltage is applied between the electrode 54 and the platform 52, and the platform is deflected downwards to let the nanofiber stand free. After several steps in loading the nanofiber, the bias voltage is removed, and the platform returns to its original height to support the nanofiber while it is being imaged with an AFM Digital Image Correlation Digital Image Correlation (DIC) is a computational method used by the invention to calculate full field surface displacements and achieve sub-pixel resolution. In this method a correlation is found between surface patterns of an object before and after deformation or motion with sub-pixel resolution that is as good, or better than, one tenth of the pixel to pixel distance one can discern by reading a picture using any conventional computer graphics program.

One Dimensional DIC

Figure 4:
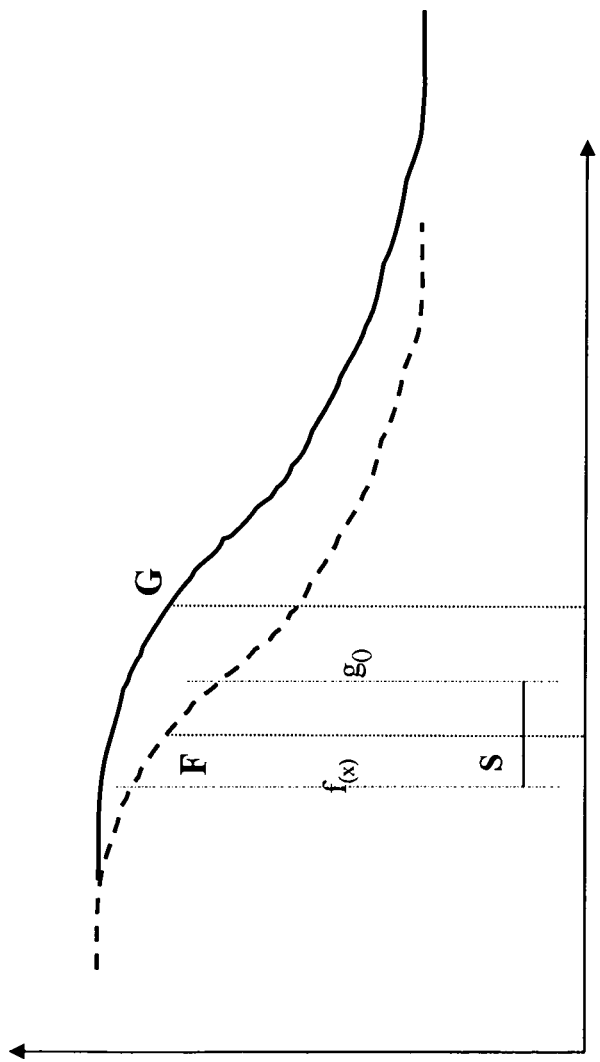
FIG. 4 illustrates two states of a line image for 1-dimensional digital image correlation (DIC) before and after deformation, denoted by F and G, respectively.

One dimensional DIC is explained in Knauss W. G., et al., Mechanics of Materials 35 pp 217-31 (2003). A simplification for 1D DIC aids understanding. In case of 1D DIC, line images (image cross-sections) are considered. Take two states of a line image before and after deformation, as shown in FIG. 4, denoted by F and G, respectively. In addition, let $f_{(x)}$ and $g_{(x)}$ define the height of an arbitrary point, x, in the undeformed and deformed states, respectively. In case of 8-bit optical digital images, the height of a point is the light intensity of the point detected by the camera in the optical microscopy, which is between 0 and $2^8-1=255$. Assume that due to deformation and/or motion, point F moved to point G. This provides the following:

$$\tilde{x} = x + u_{(x)} \qquad (1)$$

where $u_{(x)}$ is the deformation of point x. This mapping should be such that $$f_{(x)} = g^{(\tilde{x})} \qquad (2)$$

This is due to the fact that points F and G represent the same location on the sample. The objective of DIC is to find a deformation function, $u_{(x)}$, such that it can map F to G all along the region of interest. For this purpose, a nonlinear interpolation is used, which is explained below.

Let F0 at x0 be deformed to G0 at $\tilde{x}$, and S be a subset around F0. The deformation field in the subset can be written as:

$$u_{(x)} = u_{(x0)} + \left.\frac{\partial u_{(x)}}{\partial x}\right|_{x0}(x-x0) + \frac{1}{2}\left.\frac{\partial^2 u_{(x)}}{\partial^2 x}\right|_{x0}(x-x0)^2 + \ldots \qquad (3)$$

By considering small subset sizes, nonlinear terms can be omitted and the deformation can be approximated to $$u_{(x)} = u_{(x0)} + \frac{\partial u_{(x)}}{\partial x}\bigg|_{x0}(x - x0) \quad (4)$$

The mapping algorithm can now be simplified to find the proper values for the pair of $(u_{(x0)}, \partial u_{(x)}/\partial x)$, which can best map F on G. For this purpose, a least square correlation coefficient is minimized, defined as $$C = \frac{\Sigma(f_{(x)} - g_{(x)})^2}{\Sigma f_{(x)}^2} \quad (5)$$

where the summation is over all the pixels of subset S. In the case of perfect mapping, C is zero. Equations 1, 4 and 5 can be used to obtain the following expression for C.

$$C = \frac{\Sigma(f_{(x)} - g_{(x+p_1+p_2(x-x0))})^2}{\Sigma f_{(x)}^2} \quad (6)$$

where the following 2-dimensional vector is defined: $P = (u_{(x0)}, \partial u_{(x)}/\partial x|_{x0})$. To calculate the value of C at each subset in a digital image, it remains necessary to calculate the value of g at any given point in the subset, although the point might not be at the location of a pixel. This necessitates interpolation of the intensity of the points between the pixels. There are many interpolation techniques available in the art of image resizing and many of those can be used for this purpose. A preferred interpolation method for obtaining the intensity of the points between pixels is the bicubic spline interpolation scheme. The choice of the bicubic spline opens the gate to sub-pixel deformation measurement, which is the goal of the interpolation conducted in the invention.

Applying the bicubic spline technique, to find the proper value of vector P which minimizes C, equation 6 is written as a truncated Taylor series around an initial guess for P, set as P0:

$$C = C_{(P0)} + \nabla C_{(P0)}^T(P - P0) + \frac{1}{2}(P - P0)^T \nabla \nabla C_{(P0)}(P - P0) \quad (7)$$

To minimize equation 7, its derivative is set to zero. At the minimum $\nabla C_{(p0)} = 0$, so the following expression is obtained:

$$\nabla C_{(P0)} = \nabla \nabla C_{(p0)}(P - P0) \quad (8)$$

The calculation of $\nabla C_{(P0)}$ and $\nabla \nabla C_{(P0)}$ requires differentiations with respect to the components of P, which is preferably accomplished by the use of the bicubic spline interpolation. Equation 8 results in a set of two linear equations which can be solved to obtain the proper values of $P = (u_{(x0)}, \partial u_{(x)}/\partial x|_{x0})$.

Two dimensional DIC

The one dimensional DIC can be extended to two dimensional by considering the revised displacement field:

$$\tilde{x} = x + u_{(x,y)}$$

$$\tilde{y} = y + v_{(x,y)} \quad (9)$$

where u and v represent the amount of deformation at the point (x,y), respectively. The latter can be linearized as follows $$u_{(x,y)} = u_{(x0,y0)} + \frac{\partial u_{(x,y)}}{\partial x}\bigg|_{(x0,y0)}(x - x0) + \frac{\partial u_{(x,y)}}{\partial y}\bigg|_{(x0,y0)}(y - y0) \quad (10)$$

$$v_{(x,y)} = v_{(x0,y0)} + \frac{\partial v_{(x,y)}}{\partial x}\bigg|_{(x0,y0)}(x - x0) + \frac{\partial v_{(x,y)}}{\partial y}\bigg|_{(x0,y0)}(y - y0)$$

In this case, equation 6 is rewritten as:

$$C = \frac{\Sigma(f_{(x,y)} - g_{(x+p_1+p_3(x-x0)+p_5(y-y0), y+p_2+p_4(x-x0)+p_6(y-y0))})^2}{\Sigma f_{(x,y)}^2} \quad (11)$$

where the vector P is defined as:

$$P = (u_{(x0,y0)}, v_{(x0,y0)}, \partial u/\partial x|_{(x0,y0)}, \partial v/\partial x|_{(x0,y0)}, \partial u/\partial y|_{(x0,y0)}, \partial v/\partial y|_{(x0,y0)})$$

Implementation of DIC Algorithm for Measuring Displacement in Methods of the Invention To implement DIC in software for use in testing systems of the invention, the following steps are taken. First, the region of the image, which is to be correlated (and preferably includes both ends of the fiber and substantial portions of the platform surfaces), is divided to equal sections, called subsets. The subsets may overlap. The goal of DIC is to calculate the deformation and its gradients at each subset center.

Figure 5:
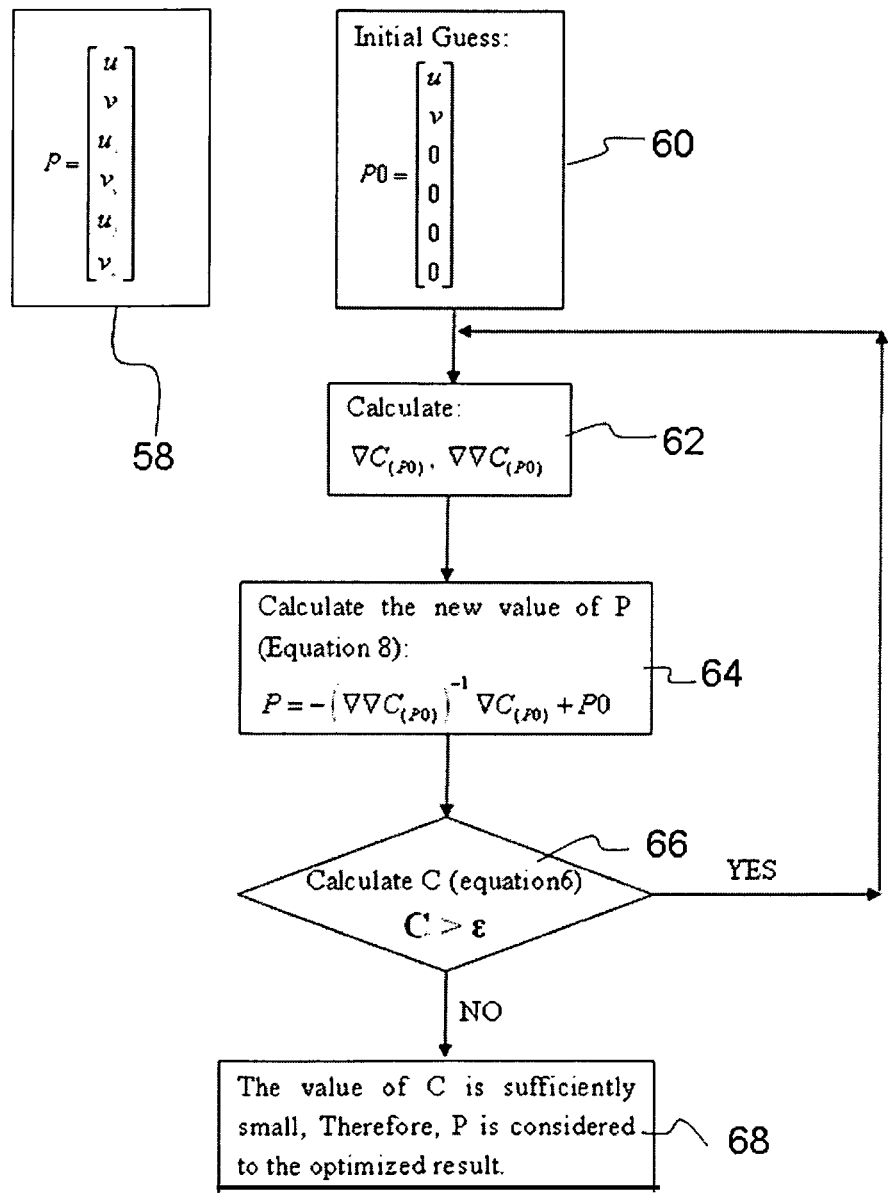
FIG. 5 is a flowchart illustrating preferred embodiment software for conducting DIC in micromechanical system for testing stress and strain of the invention.

For a first subset, a user is asked to enter a set of u and v, which represent the displacement of the first subset center in the x and y directions, respectively. Specifically, a user puts in rough estimates that can be from prior testing or from a rough measurement. Alternatively, the software can have a data table that supplies rough estimate values that are based upon the type of sample being tested. User or stored initial estimates can also be obtained by a coarse measurement of the motion of an image feature during a test by using any image software, e.g., Windows Paint. The initial estimate value can be very rough estimate, and can be a few pixels wrong (~1-2 μm). The DIC algorithm substantially improves the accuracy of the initial estimate to a fraction of a pixel (~0.06 μm or better). Thus, the initial estimate values, whether supplied by a user, prior testing data, or data tables in the software can have pixel resolution, and can have an uncertainty of a few pixels or more without impacting the accuracy of the final calculation. With reference to FIG. 5, after being initialized 58 with a rough estimate, the code finds the proper values of u and v by starting from an initial guess 60, which has the form of $P_0$, which is the initial value of the deformation vector. In step 62, the first and second gradients of the correlation coefficient, C are calculated. Then, using equation (8), an improved value for $P_0$, called P (the new deformation vector) is calculated in step 64. In step 66 C is calculated and c is defined as an upper bound for the value of C, such that any value of C below that is considered as convergence to the optimized displacement field. Typically, c is set to $10^{-5}$. In step 68, for the subsequent subsets, the value of the initial guess is set to be the value of optimized values of deformation (u,v) corresponding to the neighboring subset previously correlated, and the algorithm is repeated. The correlation is deemed complete when a predetermined value of correlation coefficient C is reached. For example, in preferred embodiments, when the correlation coefficient, C in equation 11, is below 0.00001, then the software determines that convergence to the most accurate values of the displacements have been reached. The procedure is completed when the displacements, u and v, of all pixels in the area of interest in an image are computed.

Experiments

Experiments were conducted with test cells having the form of FIG. 1. The stiffness of the test cells used in experiments was chosen based on calibration experiments with actual fibers that provided the fiber yield stress. Special care was taken so that the test cell deflections were sufficiently large to provide high force resolution in the elastic deformation regime, with the test cell motion still remaining planar. For the tests performed, the length of leaf spring beams was tuned to produce 1.3 N/m stiffness, which corresponds to a 6-μm test cell deflection at fiber yield. To perform tests with thinner fibers, the length of the beams can be increased, by depositing the Gallium stoppers closer to the anchor posts. The maximum beam length used was 400 μm, resulting in a test cell stiffness of 0.11 N/m. Assuming a minimum of 10 data points acquired before yield at 60 MPa to capture the linear response of a polymer nanofiber, and considering the fact the minimum resolved test cell deflection is 65 nm in the experiments, the estimated diameter of the thinnest fiber to be tested with this setup is 40 nm. Modifications only in the test cell dimensions but not its lay-out can be used to test nanofibers that are finer than 40 nm.

The prototype MEMS platform consistent with FIG. 1 was made of polycrystalline silicon on insulator by using conventional surface micromachining techniques developed for MEMS. Other suitable micro/nanofabrication method could also be used, and other similar MEMS materials can be used as well. The thickness of the prototype device was 6 μm, while the gap between the device and the substrate was formed by etching a 2.5-μm thick layer of silicon dioxide. With reference to FIG. 1, the steps of the example embodiment experimental test procedure were as follows:

1. A nanofiber is mounted on the free standing platforms 16, 22 using an adhesive.
2. A linear translation stage is used to attach a tipless AFM cantilever 29 to the surface 28 of the second platform. This stage is held stationary during the test, to keep one end of the sample fixed in space.
3. If large displacements (~10 μm or more) are required the suspending spring 24 can be broken before testing, which permits larger relative movements between the first and second platforms 16 and 22 and high strains in the sample.
4. The field of view of the optical microscope 30 is set so that the sample stays in view during the entire test. The rate of image recording, such as by a CCD camera, is determined by the loading rate, and the desired imaging resolution.
5. The external piezoelectric actuator is actuated to move the substrate 23.
6. The force and elongation of the nanofiber are calculated by applying digital image correlation to correlate images of platform 16, 22 and substrate 23 as the reference during the test.
7. By knowing the initial cross sectional area and length of the sample, the engineering stress strain curves of the sample can be calculated.

In the experimental application of this method of the invention, the mechanical behavior of electrospun polyacrylonitrile (PAN) nanofibers with diameters ranging from 300 nm to 600 nm was investigated. The stress-strain curves demonstrated an apparent elastic-perfectly plastic behavior with elastic modulus of 7.6±1.5 GPa and large irreversible strains that exceeded 220%. The large fiber stretch ratios were the result of a cascade of periodic necks that formed during cold drawing of the nanofibers.

The mechanical behavior of electrospun PAN nanofibers was investigated by microscale tension experiments at three nominal strain rates ($2.5 \cdot 10^{-4}$, $2.5 \cdot 10^{-3}$, $2.5 \cdot 10^{-2}$ s$^{-1}$). With a test cell consistent with FIG. 1 and a piezoelectric external actuator, large translations permitted the testing of highly elastic and strong fibers. Nanofibers were mounted on the freestanding platform grips 16, 22 by a micromanipulator and were attached with a viscous epoxy adhesive.

Several tests were conducted to ensure that the adhesive did not wet the fibers. All experiments were carried out under an optical microscope at 500× magnification. The field of view included the platforms 16 and 22 and the spring 18 so that the deflection of the test cell and the displacements of the fiber grips were extracted synchronously from optical images to compute the applied force and the fiber elongation. The test cell deflection and the fiber elongation were computed by the application of digital image correlation (DIC) on the entire device with a resolution in rigid body displacements better than 50 nm. Since the axial force in the fibers and their deformation are measured synchronously, this method for nanoscale mechanical characterization is suitable for tensile tests at various strain rates.

The stiffnesses of the test cells were calculated by a finite element analysis. An independent calibration of the test cells with pre-calibrated AFM probes according to the procedure described with response to FIG. 2 agreed with the finite element estimates. This agreement was owed to the uniform thickness of the devices and the precise determination of their dimensions. The undeformed length and diameter of each fiber were measured by optical microscopy and SEM, respectively. The fibers were not exposed to the SEM before testing to avoid embrittlement and loss of ductility, which was found to be as high as 80%. To measure the undeformed fiber, a free end of the nanofiber is not glued at the fixed platform and extends beyond the platform, and is not loaded during a test. After the experiment ends, this non-deformed segment of the fiber is imaged with an SEM to measure the initial (non-deformed) fiber diameter.

For the experiments, the MEMS test cell platform was fabricated at Case University based upon the specifications provided by the present inventors, and it was modified at the University of Illinois by using a Focused Ion Beam (FIB) to deposit stoppers to meet the requirements for testing nanofibers with specific stiffnesses. The device fabrication involved the growth of a 2.0-μm thick silicon dioxide on a (100) silicon wafer and deposition of 2.0-μm silicon dioxide by low-pressure chemical vapor deposition (LPCVD) to create a 4.0-μm thick silicon dioxide that served as sacrificial layer. Polycrystalline silicon with a thickness of 5.2 μm was deposited by LPCVD and annealed at 1050° C. to form the test cell. The polycrystalline silicon layer was patterned by photolithography, followed by plasma dry etching. The springs and platforms were released in Hydrofluoric acid to remove the undesired masking and sacrificial silicon dioxide.

The electrospun nanofibers used in the experiments were fabricated from PAN solution in dimethylformamide, with average molecular weight of 150,000. Electrospinning was conducted at 12.5 kV, at 20 cm spacing between the tip of the stainless steel tube and the bottom plate, and at feed rate of 0.2-0.5 ml/h. Nanofibers were collected on a TEM grid to facilitate their isolation, handling, and placement onto the test apparatus. All nanofibers tested originated in the same target and were subjected to the same fabrication conditions.

Figure 6:
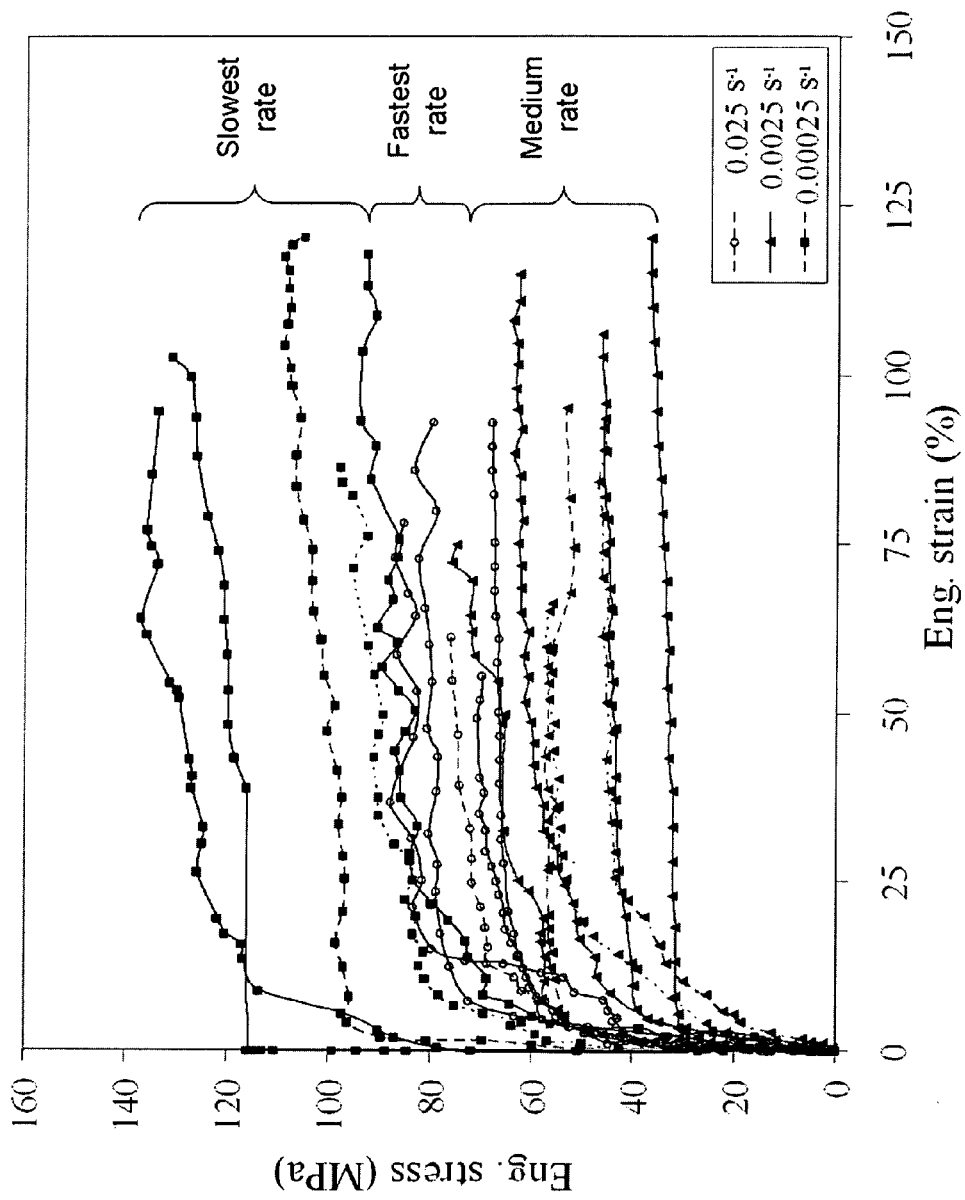
FIG. 6 show stress and strain curves engineering stress-strain curves of electrospun PAN nanofibers obtained in ambient conditions with an experimental prototype system.

The engineering stress-strain curves of a number of electrospun PAN nanofibers obtained in ambient conditions are shown in FIG. 6. The strain rates are the nominal values corresponding to the cross-head motion of the platform grips representing the strain rate after the onset of plastic deformation, i.e. when the fibers were drawn at almost constant applied force. In the elastic regime of loading, the actual strain rate was smaller than the nominal due to the simultaneous extension of the test cell. The ultimate strain at fiber failure was in the range of 60-130%, monotonically decreasing with strain rate. This behavior is generally expected because of the increased relative contribution of creep in material deformation as the strain rate is reduced. The fiber strength on the other hand was in the range of 30-130 MPa, and was in good agreement with results previously reported by others for twisted yarns of PAN, i.e. 70-160 MPa. The elastic modulus of the PAN nanofibers was 7.6±1.5 GPa, which was measured by testing longer samples (25 μm long) to improve on the strain accuracy. Contrary to the consistent trend in ultimate strain, the tensile strength did not vary monotonically with strain rate. Instead, the highest strength occurred at the slowest strain rate ($2.5 \cdot 10^{-4}$ s$^{-1}$), while the lowest strength was recorded at the medium strain rate ($2.5 \cdot 10^{-3}$ s$^{-1}$). Such behavior is unusual for homogenous material deformations, and thus, the explanation was sought in structural fiber deformations occurring as a result of the competing effects of the external loading rates and the time dependent creep and stress relaxations in the polymeric nanofibers.

The undeformed nanofibers had uniform cross sections and smooth surfaces. At the lowest strain rate, densely-packed fine ripples formed on the fibers during axial drawing. The depth of these ripples, which on average were spaced apart by 50 nm, was 20-40 nm. The average ultimate engineering strain and the true strain at failure for the samples loaded at the slowest strain rate were 110% and 127%, respectively.

The large fiber elongations at the faster strain rates were due to the formation of a cascade of deep periodic surface ripples (necks), that accommodated the displacements induced at the fiber ends. As a consequence, the nanofibers were drawn at smaller applied forces and thus engineering stresses, although the local stress (true stress) in each neck was considerably higher than the engineering stress. A lower bound of the true stress at the fiber necks at fracture is obtained by dividing the axial force in the fiber at failure by the neck cross section.

The engineering strengths of the fibers that were measured were 120 MPa and 80 MPa, respectively, while the true strengths were ~180 MPa and 230 MPa (neck section), respectively. Fibers that deformed uniformly at the slowest strain rate experienced smaller true stress at failure compared to the fibers drawn at the faster strain rates, which formed deep surface ripples.

Periodicity observed in surface ripples on the fibers requires a periodic distribution of sites that accommodate local instabilities in nanofiber deformation. Preliminary experiments pointed out to fine cracks on the fiber surface, which formed at engineering strains larger than 20%. Development of such cracks implies different surface vs. fiber core properties. Formation of surface cracks that facilitated the seeding of necks can be considered analogous to fragmentation evidenced in brittle films deposited on ductile substrates. Dense fine cracks permit the simultaneous formation of surface ripples that limit their propagation along the fiber. Neck formation is not accompanied by is neck propagation, because adjacent necks mutually limit their propagation.

SEM images were taken of fractured fibers, and indicated that the polymer molecules in the fiber core were subjected to stress conditions that resemble those in bulk materials as evidenced by the formation of voids. At the slowest strain rate, creep permitted polymer macromolecules at the fiber surface to rearrange faster than the rate of the externally applied stress, which reduced the propensity for formation of surface microcracks and subsequent local deformation instabilities. Therefore, nanofibers drawn at $2.5 \cdot 10^{-4}$ s$^{-1}$ deformed rather uniformly (homogeneously) with small fluctuations in their diameter. The lack of local structural instabilities resulted in larger axial forces in the fiber and increased engineering stress during fiber drawing as opposed to fibers that were subjected to faster loading rates.

Failure modes of the fibers that demonstrated necking are noteworthy. Contrary to macroscopic neck propagation and failure by reduction in the neck diameter, the fracture of several PAN nanofibers was owed to extrusion of a 45° cone (wedge) from the thick section of a neck. Despite the small fiber diameter, fracture due to the formation of nanopores in the fiber core, was also observed, which is expected in thick polymeric fibers and bulk polymers.

In another experiment to extract force-elongation curves, images of the MEMS device recorded during testing were compared with its unloaded configuration by DIC. In an experiment, the rigid body motions of three parts of the device were monitored: $U_1$ at the substrate, $U_2$ at the platform 16, and $U_3$ at the platform 22, which served as reference. The applied force on the fiber was then calculated as the test cell stiffness times the deflection of the test cell, which was equal to $u_f = U_2 - U_1$. The motion of the platform 16 of the test cell relative to the AFM cantilever grip 29 was used to calculate the elongation of the nanofiber, $u_f = U_2 - U_3$.

Given this measurement accuracy, relative uncertainty in the calculated quantities was computed. The uncertainty in computing the engineering strain $$\left(\varepsilon = \frac{u_f}{l_0}\right)$$

in the nanofiber is $$(\Delta\varepsilon)^2 = \left(\frac{d\varepsilon}{du}\right)^2 (\Delta u)^2 + \left(\frac{d\varepsilon}{dl_0}\right)^2 (\Delta l_0)^2 = \left(\frac{\Delta u}{l_0}\right)^2 + \varepsilon^2 \left(\frac{\Delta l_0}{l_0}\right)^2 \quad (12)$$

where $\Delta(.)$ is the uncertainty in the measurement of each independent variable. Therefore, the engineering strain in a sample with initial gage length of 25±0.5 μm is bounded to 0.26%, and it substantially improves as the sample length increases. Also, for engineering stress $$\left(\sigma = \frac{k_l u_l}{A_0}\right) : (\Delta\sigma)^2 = \left(\frac{d\sigma}{dk}\right)^2 (\Delta k)^2 + \left(\frac{d\sigma}{du_l}\right)^2 (\Delta u_l)^2 + \left(\frac{d\sigma}{dA_0}\right)^2 (\Delta A_0)^2 \quad (13)$$

$$= \sigma^2 \left(\frac{\Delta k}{k}\right)^2 + \left(\frac{k}{A_0}\right)^2 (\Delta u_l)^2 + \sigma^2 \left(\frac{\Delta A_0}{A_0}\right)^2$$

Finally, the uncertainty in computing the stiffness of the test cell $$(k_l u_l = k_c u_c) \text{ is} \tag{14}$$

$$(\Delta k_l)^2 = \left(\frac{\partial k_l}{\partial k_c}\right)^2 (\Delta k_c)^2 + \left(\frac{\partial k_l}{\partial u_l}\right)^2 (\Delta u_l)^2 + \left(\frac{\partial k_l}{\partial u_c}\right)^2 (\Delta u_c)^2$$

$$= (k_l)^2 \left(\frac{\Delta k_c}{k_c}\right)^2 + \left(\frac{k_c u_c}{u_l^2}\right)^2 (\Delta u_l)^2 +$$

$$\left(\frac{k_c}{u_l}\right)^2 (\Delta u_c)^2$$

The repeatability of three measurements of the cantilever stiffness was very good with the standard deviation of 0.03 N/m.

This relative uncertainty in engineering stress can be further reduced by improving the accuracy in the undeformed fiber cross section and by employing a compliant test cell. For an initial fiber diameter of 400±10 nm, and engineering stresses below 40 MPa, the uncertainty in engineering stress for a typical test cell with 1.5±0.15 N/m stiffness is about 4.6 MPa, which can be further reduced by improving the accuracy in the stiffness of the AFM cantilever used to calibrate the test cell.

Furthermore, if the uncertainty in the initial length and diameter of the nanofibers, and the stiffness of the test cell are negligible, such that only the uncertainties in $U_1$, $U_2$ and $U_3$ need to be considered for, equations 12 and 13 are reduced to $$\Delta \varepsilon = \frac{\Delta u}{l_0} \text{ and } \Delta \sigma = \frac{k}{A_0} \Delta u_l,$$

respectively. In this case, for a fiber with an initial length of $25^{\mu m}$, initial diameter of 400 nm, and for a test cell with the stiffness of 1.5 N/m, the uncertainties in engineering strain and stress are ~0.25% and 0.78 MPa, respectively.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A stress micro mechanical system for measuring stress and strain in micro- and nano-fibers, tubes, and wires, the system comprising:
a substrate (23) for supporting a MEMS fabrication; and
a MEMS fabrication on said substrate, said MEMS fabrication including first and second platforms having ends defining freestanding sample attachment points (16, 22), the free standing sample attachment points being biased by spring force and movable in a translation direction relative to one another with a sample attached between the sample attachment points;
an optical microscope (30) for imaging surfaces of said MEMS fabrication including a field of view encompassing both of said ends of said platforms and their entire range of movement; and
software (58-68) for conducting digital image correlation on the field of view encompassing both of said ends of said platforms and their entire range of movement in images obtained by said optical microscope to determine the movement of said surfaces at a resolution greater than the resolution of said optical microscope.

2. The system of claim 1, wherein said MEMS fabrication comprises:
a deflection spring (18, 48) anchored to said substrate and including a first free-standing platform defining a first attachment point for holding a first part of a sample to be tested,
a second free-standing platform defining a second attachment point for holding a second part of the sample.

3. The system of claim 2, wherein said MEMS fabrication further comprises stoppers (17) disposed on said substrate in a position that contributes to the stiffness of said deflection spring.

4. The system of claim 2, wherein said deflection spring comprises a generally straight beam (18) anchored on two ends by anchors attached to the substrate.

5. The system of claim 2, wherein said deflection spring comprises a U-shaped spring (48) attached by an anchor to said substrate.

6. A stress micro mechanical system for measuring stress and strain in micro- and nano-fibers tubes, and wires, the system comprising:
a substrate (23) for supporting a MEMS fabrication; and
a MEMS fabrication on said substrate, said MEMS fabrication including freestanding sample attachment points (16, 22), the free standing sample attachment points being movable in a translation direction relative to one another with a sample attached between the sample attachment points;
an optical microscope (30) for imaging surfaces of said MEMS fabrication; and
software (58-68) for conducting digital image correlation on images obtained by said optical microscope to determine the movement of said surfaces at a resolution greater than the resolution of said optical microscope, further comprising an AFM imaging platform (50) on said substrate between said freestanding sample attachment points.

7. The system of claim 6, wherein said AFM imaging platform comprises a deformable platform (52) attached to said substrate and an electrode 54 on said substrate under said platform.

8. A stress micro mechanical system for measuring stress and strain in micro- and nano-fibers, tubes, and wires, the system comprising:
a substrate (23) for supporting a MEMS fabrication; and
a MEMS fabrication on said substrate, said MEMS fabrication including free standing sample attachment points (16, 22), the free standing sample attachment points being movable in a translation direction relative to one another with a sample attached between the sample attachment points;
an optical microscope (30) for imaging surfaces of said MEMS fabrication; and
software (58-68) for conducting digital image correlation on images obtained by said optical microscope to determine the movement of said surfaces at a resolution greater than the resolution of said optical microscope, further comprising a surface (28) associated with one of said free standing attachment points and configured for attaching to a translatable probe.

9. A method for measuring stress and strain in micro- and nano- fibers, tubes, and wires, and/or measuring the force required to pull-out individual micro- and nano-fibers, tubes, and wires from a polymer matrix and therefore measure interfacial adhesion the method comprising steps of:

attaching a sample between freestanding platforms in a MEMS device;

causing relative translational movement between the platforms;

measuring motion of the platforms with an optical microscope and acquiring image data;

determining mechanical and/or adhesion properties of the sample by applying a digital image correlation algorithm to the image data.

10. The method of claim 9, wherein said measuring measures a substantial portion of surfaces of the platforms.

11. The method of claim 10, wherein said substantial portions encompass markings or irregularities on said surfaces.

12. The method of claim 9, wherein said measuring further comprises measuring motion of a substrate supporting the platforms and said determining comprises determining rigid body motions at the substrate and at each of the platforms.

13. The device of claim 1, wherein the field of view includes a portion of the substrate, and said digital image correlation comprises determining rigid body motions of said surfaces around both sample attachment points.

14. The device of claim 1, comprising a computer that stores said software on a non-transient medium and is programmed to conduct the digital image correlation.

15. A stress micro mechanical system for measuring stress and strain in micro- and nano-fibers tubes, and wires, the system comprising:

a substrate; and

MEMS means positioned on said substrate for holding and deforming a sample;

an optical microscope that images substantial surface portions in said MEMS means; and digital image correlation means for receiving images obtained by said optical microscope and for determining movement of said substantial surface portions at a resolution greater than the resolution of said optical microscope.

16. The device of claim 15, wherein said digital image correlation means determined relative rigid body displacements of device components that have said substantial surface portions.

* * * * *